US 9,521,946 B2

(12) United States Patent
Jacobsen et al.

(10) Patent No.: US 9,521,946 B2
(45) Date of Patent: Dec. 20, 2016

(54) TRANSPARENT ENDOSCOPE HEAD DEFINING A FOCAL LENGTH

(71) Applicant: Sarcos LC, Salt Lake City, UT (US)

(72) Inventors: Stephen C. Jacobsen, Salt Lake City, UT (US); Fraser M. Smith, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 0 days.

(21) Appl. No.: 14/248,184

(22) Filed: Apr. 8, 2014

(65) Prior Publication Data

US 2014/0371529 A1    Dec. 18, 2014

Related U.S. Application Data

(63) Continuation of application No. 12/487,495, filed on Jun. 18, 2009, now Pat. No. 8,690,762.

(60) Provisional application No. 61/132,566, filed on Jun. 18, 2008.

(51) Int. Cl.
  *A61B 1/00* (2006.01)
  *A61B 1/05* (2006.01)
  *A61B 1/015* (2006.01)

(52) U.S. Cl.
  CPC ......... *A61B 1/00188* (2013.01); *A61B 1/0008* (2013.01); *A61B 1/00082* (2013.01); *A61B 1/00147* (2013.01); *A61B 1/00177* (2013.01); *A61B 1/015* (2013.01); *A61B 1/05* (2013.01); *A61B 1/051* (2013.01)

(58) Field of Classification Search
  CPC ...... A61M 25/00; A61M 25/10; A61M 25/04; A61B 1/005; A61B 1/04; A61B 1/045; A61B 1/05

USPC .......................................................... 600/116
See application file for complete search history.

(56) References Cited

U.S. PATENT DOCUMENTS

| 3,787,121 | A | 1/1974 | Lowy et al. |
| 3,817,635 | A | 6/1974 | Kawahar |
| 3,856,000 | A | 12/1974 | Chikama |
| 3,886,933 | A | 6/1975 | Mori et al. |
| 3,918,438 | A | 11/1975 | Hayamizu et al. |

(Continued)

FOREIGN PATENT DOCUMENTS

| CN | 1481753 | 3/2004 |
| DE | 19742973 | 4/1998 |

(Continued)

OTHER PUBLICATIONS

Jacobsen, Stephen C., U.S. Appl. No. 10/391,489, filed Mar. 17, 2003.

(Continued)

*Primary Examiner* — Clayton E Laballe
*Assistant Examiner* — Fang-Chi Chang
(74) *Attorney, Agent, or Firm* — Thorpe North & Western LLP

(57) ABSTRACT

A catheter configured for imaging objects substantially in focus is described herein. An imaging device is disposed on the distal end of the catheter. The imaging device has an effective focal plane that is located in front of the imaging device. The catheter also includes a transparent focal instrument that has an outer periphery that is positioned at the effective focal plane of the imaging device, to enable objects in contact with the outer periphery of the transparent focal instrument to be imaged substantially in focus.

14 Claims, 8 Drawing Sheets

(56) References Cited

U.S. PATENT DOCUMENTS

| | | |
|---|---|---|
| 3,971,065 A | 7/1976 | Bayer |
| 4,277,168 A | 7/1981 | Oku |
| 4,283,115 A | 8/1981 | Fraissl |
| 4,349,456 A | 9/1982 | Sowman |
| 4,360,275 A | 11/1982 | Louderback |
| 4,403,985 A | 9/1983 | Boretos |
| 4,475,902 A | 10/1984 | Schubert |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |
| 4,585,349 A | 4/1986 | Gross et al. |
| 4,588,294 A | 5/1986 | Siegmund |
| 4,589,404 A | 5/1986 | Barath et al. |
| 4,593,313 A | 6/1986 | Nagasaki et al. |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,626,079 A | 12/1986 | Nakamura et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura et al. |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takahashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,022,972 A | 6/1991 | David et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,639 A | 6/1992 | Srivastava |
| 5,130,804 A | 7/1992 | Tamura et al. |
| 5,152,277 A * | 10/1992 | Honda ............... A61B 1/00082 600/106 |
| 5,165,063 A | 11/1992 | Strater et al. |
| 5,166,656 A | 11/1992 | Badehi et al. |
| 5,182,672 A | 1/1993 | Mukai et al. |
| 5,188,093 A | 2/1993 | Lafferty et al. |
| 5,190,523 A | 3/1993 | Lindmayer |
| 5,191,203 A | 3/1993 | McKinley |
| 5,198,894 A | 3/1993 | Hicks |
| 5,209,219 A | 5/1993 | Hollobaugh |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,408,999 A | 4/1995 | Singh et al. |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljie et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna et al. |
| 5,547,906 A | 8/1996 | Badehi |
| 5,594,497 A | 1/1997 | Ahern |
| 5,603,687 A | 2/1997 | Hori et al. |
| 5,607,435 A | 3/1997 | Sachdeva et al. |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,827,531 A | 10/1998 | Morrison et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |
| 5,904,651 A | 5/1999 | Swanson et al. |

(56) References Cited

U.S. PATENT DOCUMENTS

| | | |
|---|---|---|
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,139,819 A | 10/2000 | Unger et al. |
| 6,142,930 A | 11/2000 | Ito et al. |
| 6,161,035 A | 12/2000 | Furusawa |
| 6,184,923 B1 | 2/2001 | Miyazaki |
| 6,193,685 B1 * | 2/2001 | Goodin ............ A61M 25/1006 604/102.01 |
| 6,193,908 B1 | 2/2001 | Hampden-Smith et al. |
| 6,211,955 B1 | 4/2001 | Basiji et al. |
| 6,224,969 B1 | 5/2001 | Steenbergen et al. |
| 6,261,226 B1 | 7/2001 | McKenna et al. |
| 6,262,855 B1 | 7/2001 | Greisz |
| 6,271,206 B1 | 8/2001 | Pillai et al. |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsui et al. |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikawa |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Panescu et al. |
| 6,525,866 B1 | 2/2003 | Lin et al. |
| 6,533,722 B2 | 3/2003 | Nakashima |
| 6,537,205 B1 | 3/2003 | Smith |
| 6,551,302 B1 | 4/2003 | Rosinko et al. |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hirata et al. |
| 6,585,717 B1 | 7/2003 | Wittenberg et al. |
| 6,595,913 B2 | 7/2003 | Takahashi |
| 6,618,614 B1 | 9/2003 | Chance et al. |
| 6,622,367 B1 | 9/2003 | Bolduc et al. |
| 6,622,373 B1 | 9/2003 | Tu et al. |
| 6,624,138 B1 | 9/2003 | Tu et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogendijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,433,552 B2 | 10/2008 | Kiesel |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 | 11/2010 | Nakao |
| 7,901,870 B1 | 3/2011 | Wach |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 | 3/2002 | Schulze et al. |
| 2002/0039594 A1 | 4/2002 | Unger |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0166949 A1 | 11/2002 | Machida |
| 2002/0168776 A1 | 11/2002 | Cizdziel et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 | 6/2003 | Webler et al. |
| 2003/0197812 A1 | 10/2003 | Hirata et al. |
| 2003/0199761 A1 | 10/2003 | Yock |

(56) References Cited

U.S. PATENT DOCUMENTS

| | | |
|---|---|---|
| 2003/0202127 A1 | 10/2003 | Hirata et al. |
| 2003/0208211 A1 | 11/2003 | Kortenbach |
| 2003/0220574 A1 | 11/2003 | Markus et al. |
| 2003/0222325 A1 | 12/2003 | Jacobsen et al. |
| 2004/0006274 A1 | 1/2004 | Giller et al. |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097788 A1* | 5/2004 | Mourlas ............ A61B 1/00082 600/116 |
| 2004/0097804 A1 | 5/2004 | Sobe |
| 2004/0111031 A1 | 6/2004 | Alfano et al. |
| 2004/0115955 A1 | 6/2004 | Motoyama et al. |
| 2004/0165858 A1 | 8/2004 | Curatolo |
| 2004/0181148 A1 | 9/2004 | Uchiyama et al. |
| 2004/0222031 A1 | 11/2004 | Szalony et al. |
| 2004/0225222 A1 | 11/2004 | Zeng et al. |
| 2004/0257566 A1 | 12/2004 | Chism |
| 2004/0260148 A1 | 12/2004 | Schnitzer |
| 2005/0004453 A1 | 1/2005 | Tearney et al. |
| 2005/0054902 A1 | 3/2005 | Konno |
| 2005/0065504 A1 | 3/2005 | Melsky et al. |
| 2005/0084229 A1 | 4/2005 | Babbitt et al. |
| 2005/0088576 A1 | 4/2005 | Hirata et al. |
| 2005/0099824 A1 | 5/2005 | Dowling et al. |
| 2005/0110892 A1 | 5/2005 | Yun |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0171521 A1 | 8/2005 | Brucker et al. |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0226636 A1 | 10/2005 | Hiramatsu et al. |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | O'Connor |
| 2006/0079835 A1 | 4/2006 | Frassica |
| 2006/0106283 A1 | 5/2006 | Wallace et al. |
| 2006/0135921 A1 | 6/2006 | Wiercinski et al. |
| 2006/0142700 A1 | 6/2006 | Sobelman et al. |
| 2006/0146172 A1 | 7/2006 | Jacobsen et al. |
| 2006/0161048 A1 | 7/2006 | Squicciarini |
| 2006/0181774 A1 | 8/2006 | Ojima et al. |
| 2006/0252994 A1 | 11/2006 | Ratnakar |
| 2006/0253088 A1 | 11/2006 | Chow et al. |
| 2007/0010709 A1* | 1/2007 | Reinschke ............ 600/116 |
| 2007/0032796 A1 | 2/2007 | Chin-Chen et al. |
| 2007/0066869 A1* | 3/2007 | Hoffman ............ 600/121 |
| 2007/0073321 A1 | 3/2007 | Mikkaichi et al. |
| 2007/0083232 A1 | 4/2007 | Lee |
| 2007/0088276 A1 | 4/2007 | Stubbs et al. |
| 2007/0135803 A1 | 6/2007 | Belson |
| 2007/0146887 A1 | 6/2007 | Ikeda et al. |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0058601 A1 | 3/2008 | Fujimori |
| 2008/0071141 A1 | 3/2008 | Gattani et al. |
| 2008/0094326 A1 | 4/2008 | Yamaki et al. |
| 2008/0114309 A1 | 5/2008 | Zuckerman |
| 2008/0143822 A1 | 6/2008 | Wang et al. |
| 2008/0160257 A1 | 7/2008 | Takada et al. |
| 2008/0177141 A1* | 7/2008 | Wu et al. .............. 600/112 |
| 2008/0183080 A1 | 7/2008 | Abraham |
| 2008/0188767 A1 | 8/2008 | Oaki et al. |
| 2008/0227893 A1 | 9/2008 | Tamori et al. |
| 2008/0267562 A1 | 10/2008 | Wang et al. |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1* | 3/2009 | Ichimura et al. ............ 600/109 |
| 2009/0119808 A1 | 5/2009 | Giakos |
| 2009/0137928 A1 | 5/2009 | Quick et al. |
| 2009/0143645 A1 | 6/2009 | Matthes |
| 2009/0155371 A1 | 6/2009 | Sojka et al. |
| 2009/0156899 A1 | 6/2009 | Konishi |
| 2009/0180197 A1 | 7/2009 | Jacobsen et al. |
| 2009/0213894 A1 | 8/2009 | Grapov et al. |
| 2009/0234325 A1 | 9/2009 | Rozenberg et al. |
| 2009/0267270 A1 | 10/2009 | Murakami et al. |
| 2009/0287048 A1* | 11/2009 | Jacobson et al. ............ 600/109 |
| 2009/0306474 A1 | 12/2009 | Wilson |
| 2010/0016662 A1 | 1/2010 | Salsman et al. |
| 2010/0085567 A1 | 4/2010 | Dottery et al. |
| 2010/0106134 A1 | 4/2010 | Jolly et al. |
| 2010/0134872 A1 | 6/2010 | Johnson et al. |
| 2010/0171821 A1 | 7/2010 | Jacobsen et al. |
| 2010/0188492 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482997 | 10/1991 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | S61-261713 | 11/1986 |
| JP | 63-155115 | 6/1988 |
| JP | H01-282514 | 11/1989 |
| JP | H05-039501 | 2/1993 |
| JP | 5 -049602 | 3/1993 |
| JP | H05-197828 | 8/1993 |
| JP | H07-148105 | 6/1995 |
| JP | H07-222712 | 8/1995 |
| JP | 08076028 | 3/1996 |
| JP | 08084700 | 4/1996 |
| JP | H09-021963 | 1/1997 |
| JP | 11 137512 | 5/1999 |
| JP | 2001008083 | 1/2001 |
| JP | 2001314365 | 11/2001 |
| JP | 2004004929 | 1/2004 |
| JP | 2004086553 | 3/2004 |
| JP | 2004094873 | 3/2004 |
| JP | 2004329700 | 11/2004 |
| JP | 2005006725 | 1/2005 |
| JP | 2005334462 | 8/2005 |
| JP | 2005533530 | 11/2005 |
| JP | 2006162418 | 6/2006 |
| JP | 2006314459 | 11/2006 |
| JP | 2006320369 | 11/2006 |
| JP | 2007167387 | 7/2007 |
| JP | 2007312290 | 11/2007 |
| JP | 2009067946 | 4/2009 |
| KR | 10-20080027935 | 3/2008 |
| WO | WO 98/38907 | 9/1998 |
| WO | WO 99/40624 | 8/1999 |
| WO | WO 00/54033 | 9/2000 |
| WO | WO 03/081831 | 10/2003 |
| WO | WO 2006/060777 | 6/2006 |
| WO | WO 2007008876 | 1/2007 |
| WO | WO 2007138889 A1 * | 12/2007 ............ G02B 23/24 |

(56) References Cited

FOREIGN PATENT DOCUMENTS

OTHER PUBLICATIONS

Jacobsen, Stephen C., U.S. Appl. No. 10/391,490, filed Mar. 17, 2003.
Jacobsen, Stephen C., U.S. Appl. No. 10/391,513, filed Mar. 17, 2003.
Jacobsen, Stephen C., U.S. Appl. No. 11/292,902, filed Dec. 1, 2005.
Jacobsen, Stephen C., U.S. Appl. No. 11/810,702, filed Jun. 5, 2007.
Jacobsen, Stephen C., U.S. Appl. No. 12/008,486, filed Jan. 11, 2008.
Jacobsen, Stephen C., U.S. Appl. No. 12/079,741, filed Mar. 27, 2008.
Jacobsen, Stephen C., U.S. Appl. No. 12/152,730, filed May 16, 2008.
Jacobsen, Stephen C., U.S. Appl. No. 12/487,481, filed Jun. 18, 2009.
Jacobsen, Stephen C., U.S. Appl. No. 12/512,188, filed Jul. 30, 2009.
Jacobsen, Stephen C.; U.S. Appl. No. 12/611,776, filed Nov. 3, 2009.
Jacobsen, Stephen C.; U.S. Appl. No. 12/792,562, filed Jun. 2, 2010.
Jacobsen, Stephen C.; U.S. Appl. No. 12/896,731, filed Oct. 1, 2010.
Jacobsen, Stephen C.; U.S. Appl. No. 12/896,732, filed Oct. 1, 2010.
Jacobsen, Stephen C.; U.S. Appl. No. 12/896,737, filed Oct. 1, 2010.
Jacobsen, Stephen C.; U.S. Appl. No. 12/896,743, filed Oct. 1, 2010.
Jacobsen, Stephen C.; U.S. Appl. No. 12/938,672, filed Nov. 3, 2010.
Jacobsen, Stephen C.; U.S. Appl. No. 12/946,442, filed Nov. 15, 2010.
Notice of Allowance for U.S. Appl. No. 12/611,776 dated Mar. 17, 2015, 18 pages.
Notice of Allowance for U.S. Appl. No. 12/896,732 dated May 18, 2015, 6 pages.
Notice of Allowance for U.S. Appl. No. 12/938,672 dated May 6, 201, 39 pages.
Notice of Allowance for U.S. Appl. No. 13/940,791 dated Oct. 28, 2015, 12 pages.
Office action for U.S. Appl. No. 12/896,731 dated Jan. 27, 2015, 19 pages.
Office action for U.S. Appl. No. 12/896,731 dated Jun. 26, 2014, 18 pages.
Office action for U.S. Appl. No. 12/896,731 dated Sep. 2, 2015, 14 pages.
Office action for U.S. Appl. No. 13/940,791 dated Jan. 5, 2015, 31 pages.
Office action for U.S. Appl. No. 13/940,791 dated Jun. 27, 2014, 38 pages.
Office action for U.S. Appl. No. 13/940,791 dated May 8, 2015, 28 pages.
Office action for U.S. Appl. No. 13/966,030 dated Aug. 6, 2015, 28 pages.
PCT Application PCT/US2010/051188; filed Oct. 1, 2010; Stephen C. Jacobsen; International Search Report mailed Jul. 13, 2011.
PCT Application PCT/US2010/051192; filed Oct. 1, 2010; Stephen C. Jacobsen; ISR mailed May 30, 2011.
PCT Application PCT/US2010/051198; filed Oct. 1, 2010; Stephen C. Jacobsen; ISR mailed Jun. 3, 2011.
PCT Application PCT/US2010/051200; filed Oct. 1, 2010; Stephen C. Jacobsen; ISR mailed Jun. 3, 2011.
Subrahmanyam et al, "A Text Book of Optics", XP055126947, Jan. 2004, ISBN: 978-8-12-192611-9, pp. 199-200, Retrieved on Jul. 4, 2014.
Tsuchida et al., "Design of Imaging Lens Systems That Use Low Dispersive Radial Gradient-Index Rod", Jun. 1998, pp. 3633-3637, vol. 37, No. 6B, Fig. 1,7,9, Japan Journal Appl. Phys., Japan.
U.S. Appl. No. 12/487,481, filed Jun. 18, 2009; Stephen C. Jacobsen; office action dated Oct. 12, 2012.
U.S. Appl. No. 12/512,188, filed Jul. 30, 2009; Stephen C. Jacobsen; office action dated Nov. 19, 2012.
U.S. Appl. No. 12/152,730, filed May 16, 2008; Stephen C. Jacobson; office action issued Sep. 16, 2011.
Anonymous: "In vivo—Wikipedia, the free encyclopedia", Sep. 27, 2007 (Sep. 27, 2007), XP055244092, Retrieved from the Internet: URL:http://web.archive.org/web/20070927001435/http://en.wikipedia.org/wiki/In_vivo [retrieved on Jan. 22, 2016].
J. C. Jung: "In Vivo Mammalian Brain Imaging Using One- and Two-Photon Fluorescence Microendoscopy", Journal of Neurophysiology, val. 92, No. 5, Jul. 7, 2004 (Jul. 7, 2004), pp. 3121-3133.

\* cited by examiner

TRANSPARENT ENDOSCOPE HEAD DEFINING A FOCAL LENGTH

PRIORITY

This application is a continuation of U.S. Ser. No. 12/487,495 filed on Jun. 18, 2009 entitled, "Transparent Endoscope Head Defining a Focal Length" and given patent number U.S. Pat. No. 8,690,762 claims priority to U.S. Provisional Ser. No. 61/132,566 filed on Jun. 18, 2008 entitled "Transparent Endoscope Head Defining a Focal Length" which are both incorporated herein by reference in their entirety.

FIELD OF THE INVENTION

The present invention relates to medical devices, and more particularly to miniaturized in-situ imaging devices and methods of operation of said devices.

BACKGROUND

The present invention relates generally to the field of endoscopy. More particularly, the present invention relates to improved endoscopic and catheter imaging.

Small imaging devices have become particularly useful in medical diagnostic and treatment applications. Portions of human anatomy previously viewable only by a surgical procedure can be viewed now by a minimally invasive catheterization, provided an imaging device can be made that is small enough to view the target anatomy.

Other uses for very small imaging devices are recognized. For example, such devices can be used and are desirable for surveillance applications, for monitoring of conditions and functions within devices, and for size and weight-critical imaging needs as are present in aerospace applications, to name a few.

While the present invention has applications in these aforementioned fields and others, the medical imaging application can be used to favorably illustrate unique advantages of the invention. The desirability of providing imaging at sites within the anatomy of living creatures, especially humans, distal of a small orifice or luminal space has long been recognized. A wide variety of types and sub-types of endoscopes have been developed for this purpose, One advance in imaging technology which has been significant is the increased reduction of individual component sizes. Presently, charged coupled devices (CCD) such as miniature cameras can be manufactured so as to fit on the end of a catheter approximately the size of a couple of strands of wire. Lenses, optical fiber, and miniature surgical equipment can also be produced in miniature dimensions. However, these devices although functional and increasingly effective, can be difficult to position in order to appropriately image small areas of a target tissue.

For example, small cell carcinoma tends to start in the larger breathing tubes of the lungs. In its early stages it may only affect a small number of cells, covering a distance of only 20-40 microns across. Because it could be advantageous to image and diagnose this problem in this early stage before it rapidly grows and becomes quite large it is important to be able to access, locate and image these small areas. High resolution imaging can effectively view these cells if such locations can be found and if the imaging device can be appropriately positioned, focused, and imaged. This process is increasingly complicated in cases, such as small cell carcinoma, wherein the cell clusters are located in large passageways. While a larger endoscope could be used for this procedure, a small catheter will substantially minimize patient trauma and duress. Presently, a user will be required to repeatedly move a small catheter or endoscope forward-and-backward, side-to-side in a trial and error fashion in attempts to acquire the target area within focus of the miniature camera. Typically, this process results in images that are not in complete focus and that can be difficult to diagnose.

SUMMARY

It has been recognized that it would be advantageous to develop a catheter that can be easily and effectively positioned so that a target object can be imaged substantially in focus.

Briefly, and in general terms, the invention is directed to a catheter configured for imaging objects substantially in focus. An imaging device is disposed on the distal end of the catheter. The imaging device has an effective focal plane that is located in front of the imaging device. The catheter also includes a transparent focal instrument that has an outer periphery that is positioned at the effective focal plane of the imaging device, to enable objects in contact with the outer periphery of the transparent focal instrument to be imaged substantially in focus.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

FIG. 8 is a perspective view of one embodiment of the imaging device of FIG. 2a.

Figure 1:
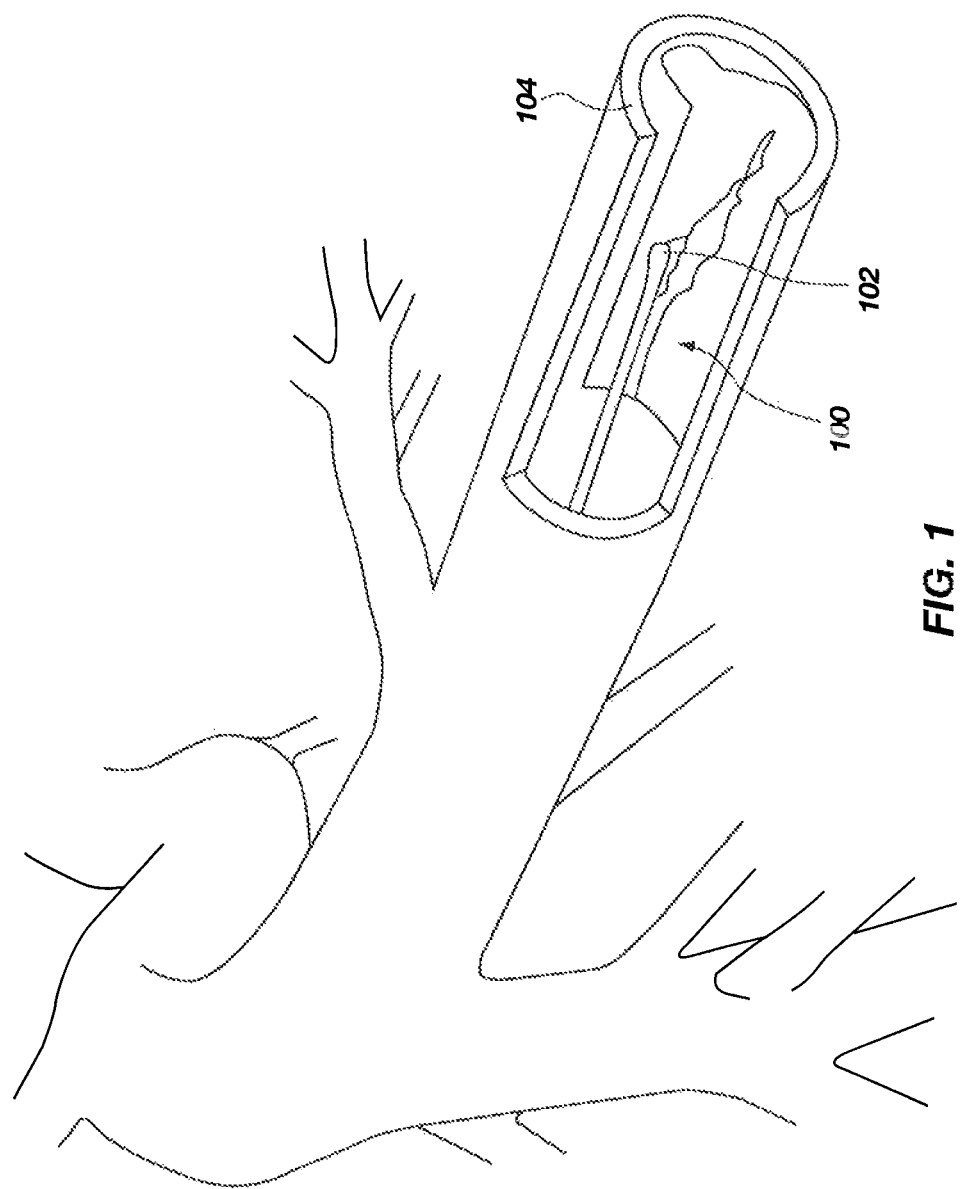
FIG. 1 is a schematic illustration of an exemplary catheter in accordance with principles of the invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention, as represented in FIGS. 1 through 9, is not intended to limit the scope of the invention, as claimed, but is presented for purposes of illustration only and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout. In describing and claiming the present invention, the following terminology will be used.

The singular forms "a," "an," and "the" include plural referents unless the context clearly dictates otherwise. Thus, for example, reference to "a camera device" includes reference to one or more of such camera devices, and reference to "an inflatable balloon" includes reference to one or more of such inflatable balloons.

As used herein, "catheter" refers to any one of a variety of catheter or endoscopic systems designed to imaging within the anatomy of living creatures or other appropriate system wherein imaging, surveillance, or other need is present. In one embodiment the catheter can comprise a miniature catheter having a SSID chip and a GRIN lens for imaging small locations with high resolution. Other imaging systems can be incorporated as will be apparent to one of ordinary skill in the art.

As used herein, "effective focal plane" or "main focal plane" refers to forward location in front of a camera/imaging device at which an object(s) is/are substantially in sharp focus or "in focus". It is not intended that this location be a single point in space, rather it is intended that this focal point refer to the two or three-dimensional area in which an imaging device can image an object substantially in focus. An object imaged at this distance from the camera, given the proper lighting conditions, can have higher resolution and increased clarity than an object imaged at a closer or further distance. This effective focal plane will vary with different camera and imaging devices, as will be appreciated by one of ordinary skill in the art.

As used herein, "imaging device" refers to any one of the variety of catheter and endoscopic imaging devices, camera systems, fiber bundles, and other such devices known in the art. For example, the imaging device can include a SSID having an imaging array and a lens, as will be described in greater detail below.

As used herein, "solid state imaging device" or SSID in the exemplary embodiments generally comprises an imaging array or pixel array for gathering image data, and can further comprise conductive pads electrically coupled to the imaging array, which facilitates electrical communication therebetween. In one embodiment, the SSID can comprise a silicon or other semiconductor substrate or amorphous silicon thin film transistors (TFT) having features typically manufactured therein. In another embodiment, the SSID can comprise a non-semiconductor substrate coated with a semiconductor material, or other equivalent structure. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the affects of a more traditionally shaped lens. In one embodiment, this is referred to as a GRIN rod lens. However, use of other suitable GRIN lens systems is contemplated for use herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

With reference to FIG. 1, the invention is embodied in a catheter, shown generally at 100, including an imaging device and a transparent focal instrument 102 coupled to the catheter 100, at a distal tip of the catheter 100. The transparent fiscal instrument 102 has an outer periphery that is positioned at the effective focal plane of the imaging device. As shown, the outer periphery of the transparent focal instrument 102 can be placed in contact with bodily tissue 104 so that the bodily tissue can be in position to be "in focus" for imaging.

Because a target bodily tissue can be located in a relatively large bodily passage and because the catheter 100 is relatively small, as shown in FIG. 1, it is often difficult to position the catheter 100 in proper position, such as in the free space of a large bodily passage, so that it can position the target area "in focus" with respect to the camera. However, due to the nature of catheter systems the distal end of a catheter is frequently in contact with bodily tissue as it is directed along curved bodily passages and cavities. When a semi-flexible catheter is directed along a bodily passage, for example, the lungs, veins, or gastrointestinal (GI) tract, the distal end of the catheter will typically be in contact with the outer edge of these passages when being directed around a turn. At these points of contact, the catheter having the transparent focal instrument can effectively image the outer walls of these passages in detailed and accurate focus.

Figure 8:
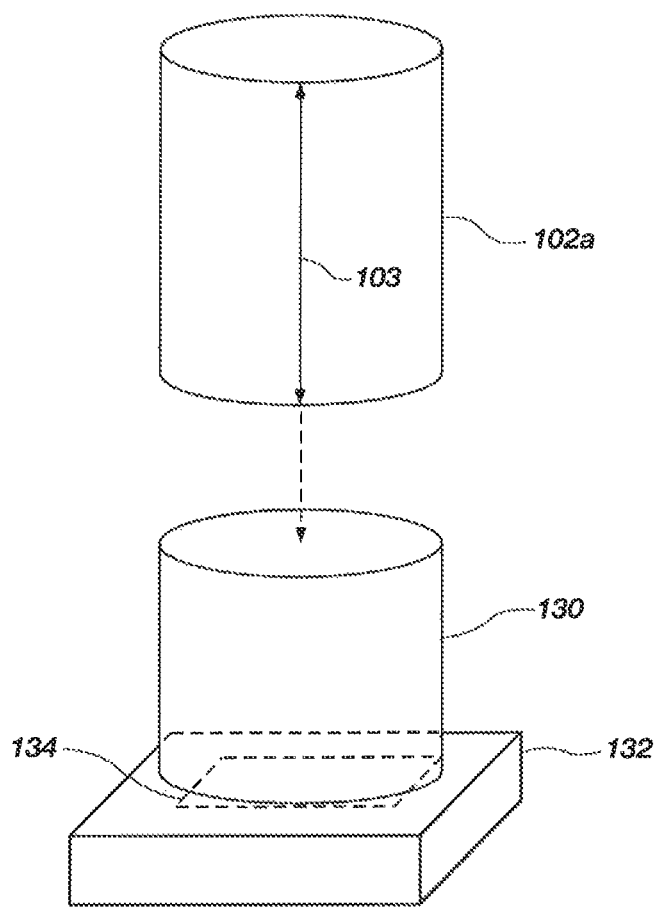

The imaging device can include various camera and lens devices. In one exemplary embodiment the imaging device can include a SSID chip 132 and GRIN rod lens 130, as shown in FIG. 8. The SSID 132 can comprise a silicon or other semiconductor substrate or amorphous silicon thin film transistors (TFT) having features typically manufactured therein. In another embodiment, the SSID 132 can comprise a non-semiconductor substrate coated with a semiconductor material, or other equivalent structure. Features including the imaging array 134, the conductive pads (not shown), metal traces (not shown), circuitry (not shown), etc., can be fabricated therein. With respect to the conductive pads, the connection between conductive pads and a conductive line of an umbilical or catheter body can be through soldering, wire bonding, solder bumping, eutectic bonding, electroplating, and conductive epoxy. However, a direct solder joint having no wire bonding between the electrical umbilical and the conductive pads can be preferred as providing good steerability can be achieved with less risk of breaking electrical bonding. In one embodiment, the conductive line of the umbilical can provide power, ground, clock signal, and output signal with respect to the SSID 132. Other integrated circuit components can also be present for desired applications, such as light emitting diodes (LEDs), for providing light to areas around the GRIN rod lens 130.

It is not required that all of these components be present, as long as there is a visual data gathering and sending image device present, and some means provided to connect the data gathering and sending device to a visual data signal processor. Other components, such as the umbilical, housing, adaptors, utility guides, and the like, can also be present, though they are not shown in FIG. 8. The SSID 132 can be any solid state imaging device, such as a CCD, a CID, or a CMOS imaging device. Also, the GRIN rod lens 130 can be coated with an opaque coating on the curved surface to prevent light from entering the lens at other than the flat surface that is most distal with respect to the SSID 132. Additional principles of operation and details of construction of similar micro-camera assemblies can be found in U.S. patent application Ser. Nos. 10/391,489, 10/391,490, 11/292,902, and 10/391,513 each of which are incorporated herein by reference in their entireties.

Figure 2A:
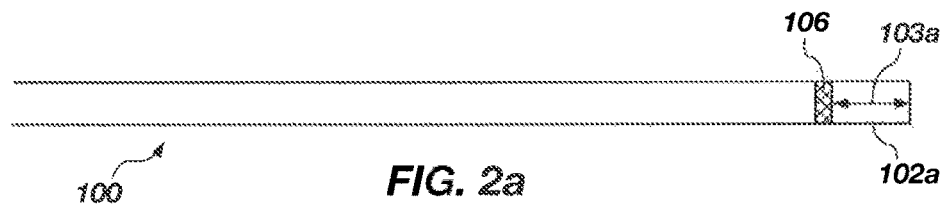
FIG. 2a is a side view of one embodiment of the catheter of FIG. 1.
Figure 2B:
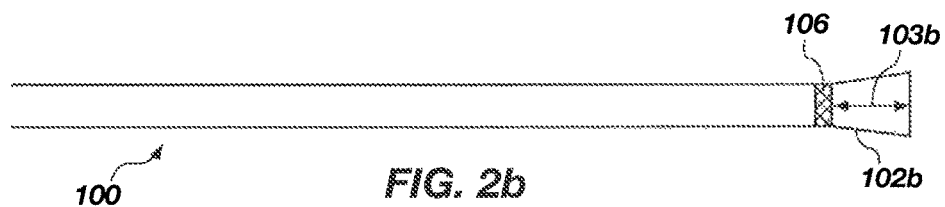
FIGS. 2b-2d are side views of other embodiments of the catheter of FIG. 1.
Figure 2C:
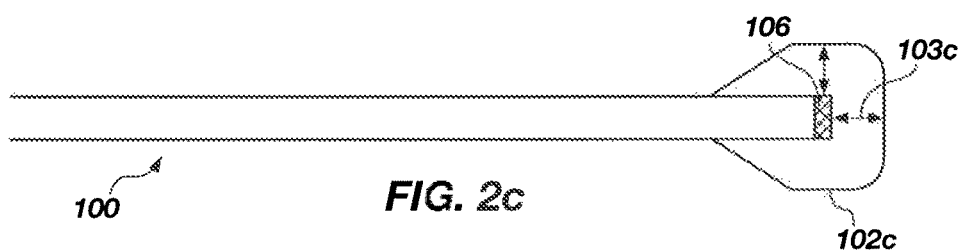
Figure 2D:
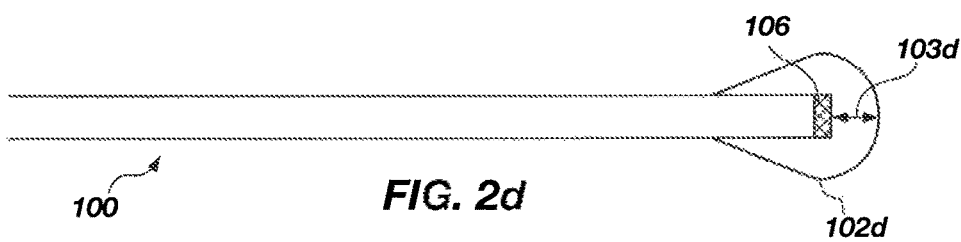

Reference will now be made to FIGS. 2a-3b, which depict various embodiments of transparent focal instruments, in accordance with the principles of the invention. The catheter 100 includes an imaging device 106. A transparent focal instrument 102 is coupled to the camera, for instance, the transparent focal instrument 102 can be coupled to the imaging device 106, as shown in FIGS. 2a-2b, or coupled to the catheter body as shown in FIGS. 2c-3b. The transparent focal instrument 102 is configured to have an outer periphery that is positioned at a distance approximately equal to the distance from the imaging device 106 to the effective focal plane of the imaging device 106. This distance is represented at 103.

As different camera systems can have varying angles of view, the transparent focal instrument can have respectively varied shapes, contours, lengths, and other such properties. The exemplary embodiments of FIGS. 2a-3b are intended to be presented herein as examples and are not intended to be all inclusive regarding the type, shape, or dimensions of potential transparent focal instruments.

The transparent focus instrument 102 can be a hollow spacer, solid spacer, inflatable or inflated balloon, or other such device as will be apparent to one of ordinary skill in the art. The spacer can be composed of glass or a transparent polymer which includes common transparent plastics such as polystyrene, polycarbonate, or PET.

Figure 3A:
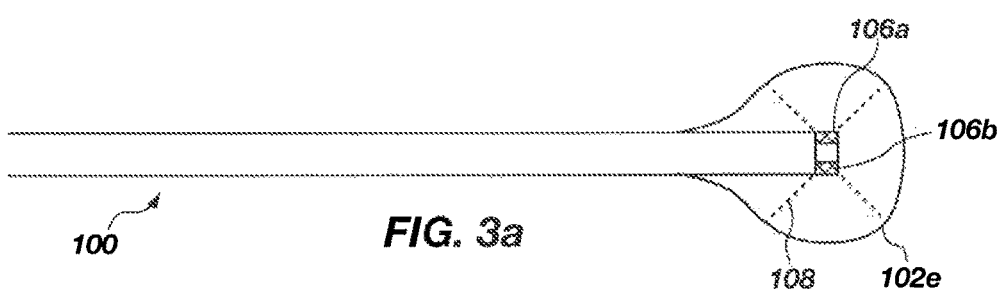
FIGS. 3a-3b are side views of yet other embodiments of the catheter of FIG. 1.
Figure 3B:
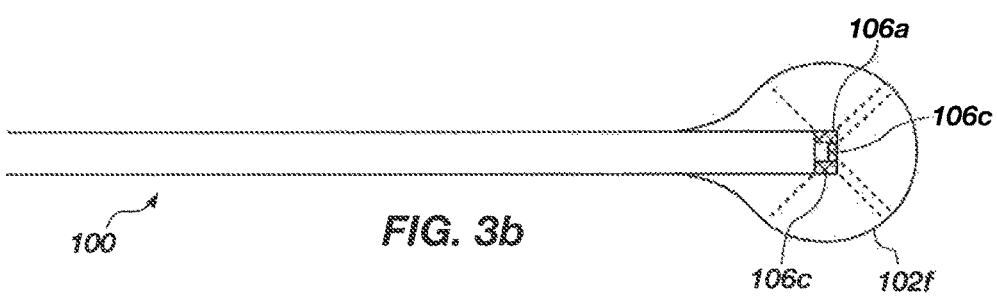

Multiple imaging devices 106 can be included on a single catheter 100, as shown in FIGS. 3a-3b. Accordingly, the transparent focus instrument 102 can be configured to have an outer periphery at the effective focal plane of each imaging device 106. When conducting certain endoscopic procedures it may be advantageous to include imaging devices that can image in lateral directions. Typically, catheter devices have a limit to the flexibility of the catheter body which limits the device's ability to turn and face a lateral object when in small or narrow passageways. As such, by including an imaging device that faces in one or more lateral directions as well as one or more transparent focal instruments, respectively, the catheter can be directed down a narrow passage of the body while imaging "in focus" the wall of the bodily passage.

In another embodiment the catheter 100 can include a turning device, as is known in the art. The turning device (not shown) can assist the catheter 100 to be directed to a target area of the body as well as turning the distal end of the catheter 100, including the imaging device 106 and transparent focal instrument 102 towards a target object or area. This turning device can assist a user to accurately position the periphery of the transparent focal instrument 102 in contact with a desired tissue.

Figure 4:
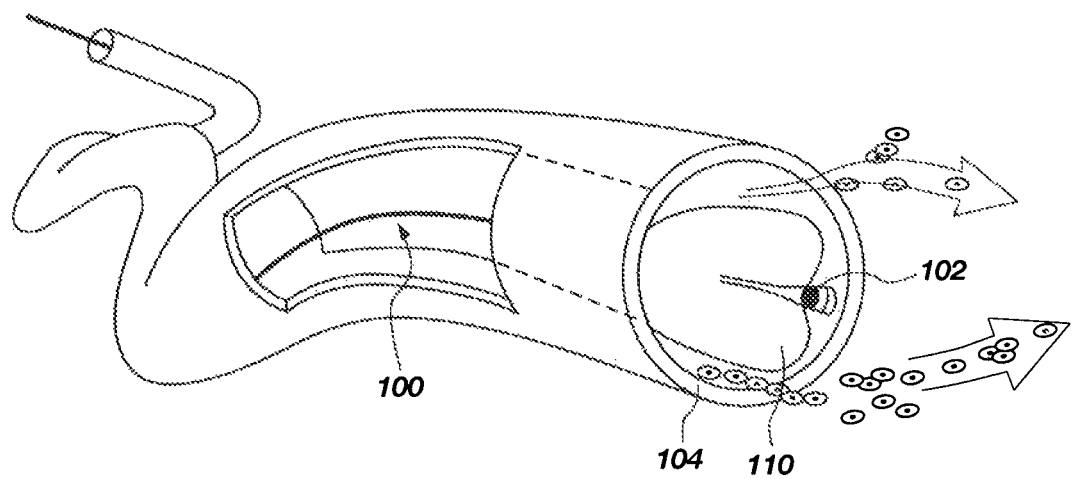
FIG. 4 is a schematic illustration of a catheter having an inflatable balloon to position the imaging device in accordance with one embodiment of the invention.

FIG. 4 depicts the catheter 100 according to one embodiment of the present invention, being directed through a bodily passage 104. In this exemplary situation, the bodily passage 104 is substantially larger than the catheter 100 such that the transparent focal instrument 102 is not naturally in contact with the passage wall. An inflatable balloon 110, coupled to the catheter 100, which can be inflated to force the transparent focal instrument 102 in contact with the passage wall. Such a balloon can be designed and constructed by methods and materials currently known in the art.

Figure 6A:
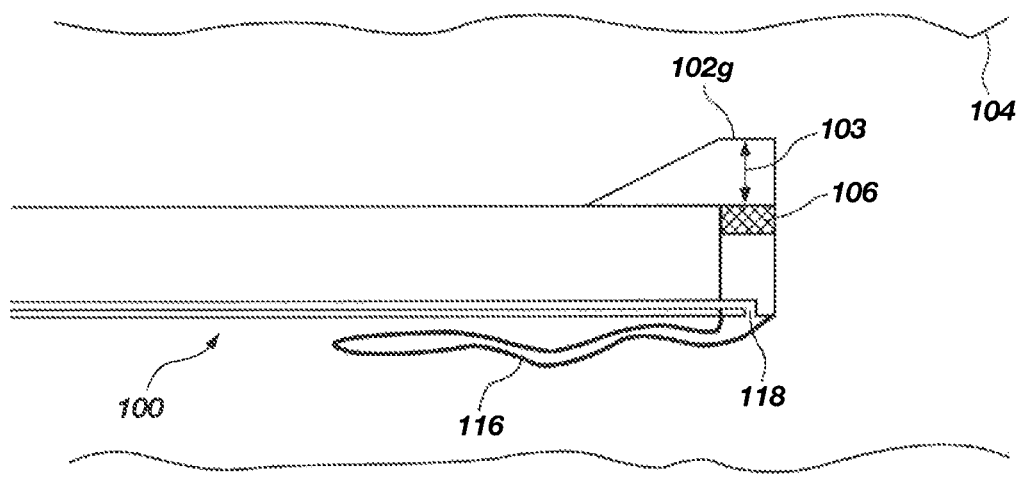
FIGS. 6a and 6b are side views of one embodiment of the catheter of FIG. 4.
Figure 6B:
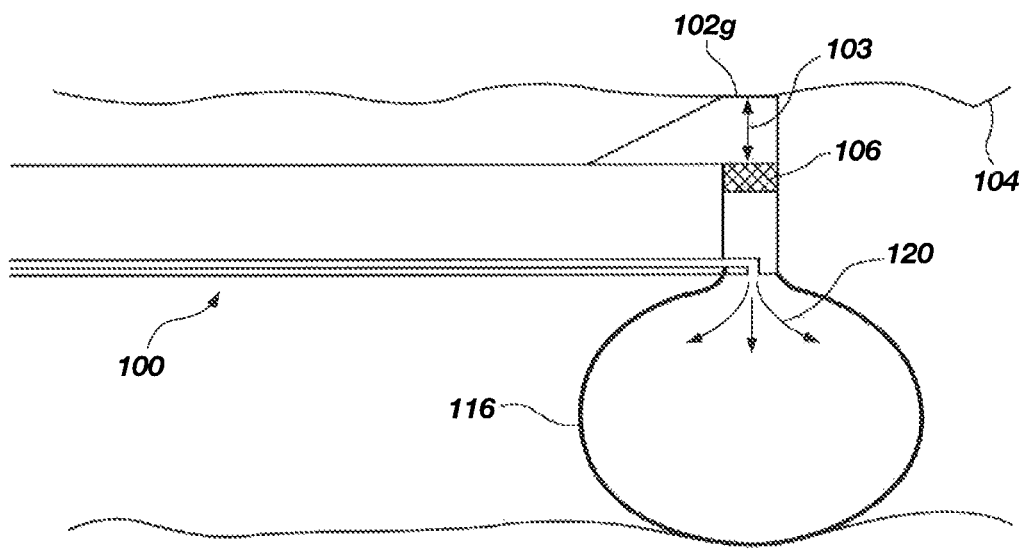

FIGS. 6a-6b illustrate a function of the inflatable balloon 116 represented in FIG. 4. As shown, the catheter 100 can include a laterally-oriented imaging device 106 having a transparent focal instrument 102g. The inflatable balloon 116 is disposed on the side opposite the imaging device 106 and is attached to a fluid source 118 configured to inflate and deflate the balloon 116 with a fluid. As shown in FIG. 6a, the transparent focal instrument 102g is not initially in contact with the bodily passage wall 104. FIG. 6b shows a fluid 120 being inserted into the balloon. The fluid 120 can include air, oxygen, saline solution, or other fluid known in the art. As the balloon 116 is filled with the fluid 120, the transparent focal instrument 102g is positioned in contact with the passage wall 104. As will be apparent, the balloon 116 can include a variety of shapes and sizes according to the needs of the user. In one embodiment, the balloon 116 can be non-spherically shaped when inflated, to allow the passage of fluids within the bodily passage, as shown in FIG. 4. In another embodiment, the catheter 100 can include more than one inflatable balloon 116, which can each selectively be inflated to position the transparent focal instrument 102g in contact with a target object/location. In another embodiment, the balloon 116 comprises a toroidal or torus structure to allow the passage of fluids through the otherwise occluded vessel.

Figure 6C:
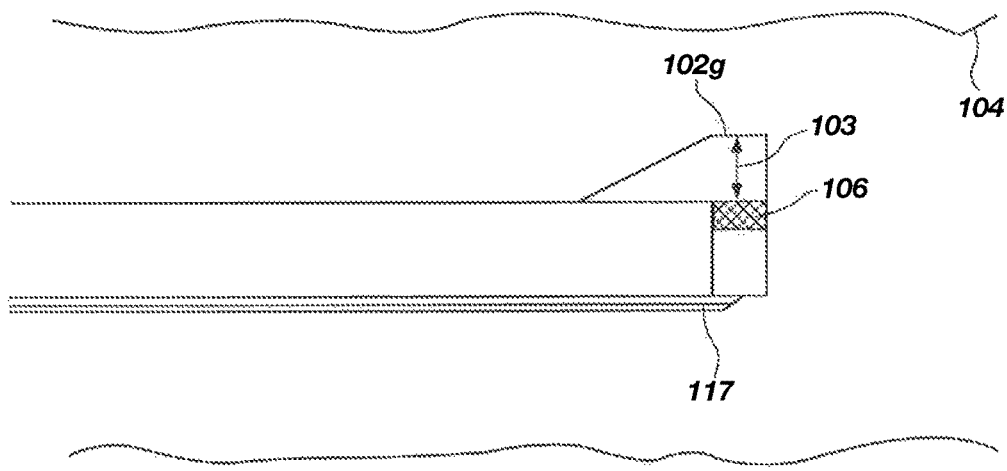
FIGS. 6c and 6d are side views of an additional embodiment of the catheter of FIG. 4.
Figure 6D:
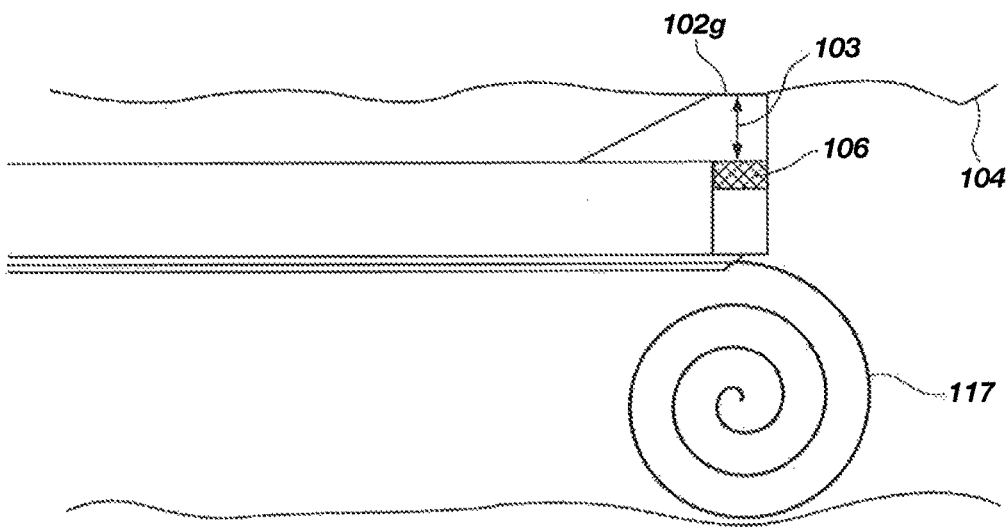

Referring now to FIGS. 6c through 6d, a different method of laterally positioning the transparent focal instrument 102g is illustrated. In this embodiment the balloon shown in FIGS. 6a and 6b is replaced with a piece of preformed wire 117, which when extended from the catheter 100 forms a coil which moves the transparent focal instrument 102g into contact with a target object/location. In one embodiment, the preformed wire 117 comprises a shape memory alloy such as Nitinol. In one aspect of the invention a plurality of imaging devices 106 may be disposed lengthwise along a side of the catheter body with corresponding focal instruments 102g and positioning devices. In this manner, a practitioner may capture numerous images of an interior of a patient as the catheter 100 is advanced within the patient.

Figure 5:
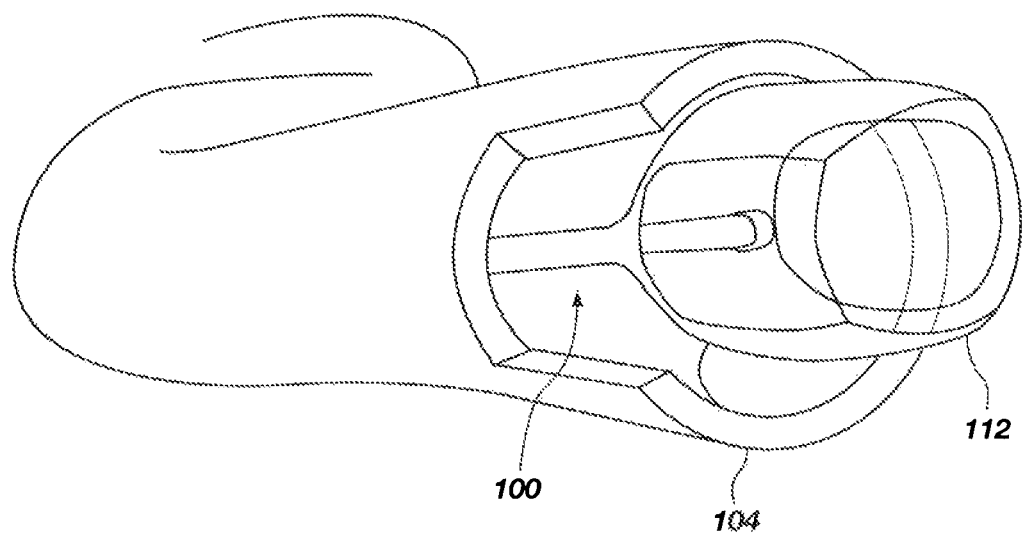
FIG. 5 is a schematic illustration of an exemplary catheter having an inflatable balloon as a transparent focal instrument, in accordance with one embodiment of the invention.

FIG. 5 depicts the catheter 100 according to one embodiment of the present invention, wherein the transparent focal instrument is in the form of a transparent inflatable balloon 112. When inflated the transparent inflatable balloon 112 has an outer periphery that is positioned at the effective focal plane of the imaging device, to enable objects in contact with the outer periphery of the transparent focal instrument to be imaged substantially in focus. The use of a flexible, transparent balloon 112 as a transparent focal instrument allows the catheter to maintain miniature dimensions due to the relatively low volume and flexibility of the balloon. Additionally, the transparent balloon 112 can act as an optical environment for the imaging device, displacing the fluids and other material that can obstruct the imaging path of the imaging device.

Figure 7A:
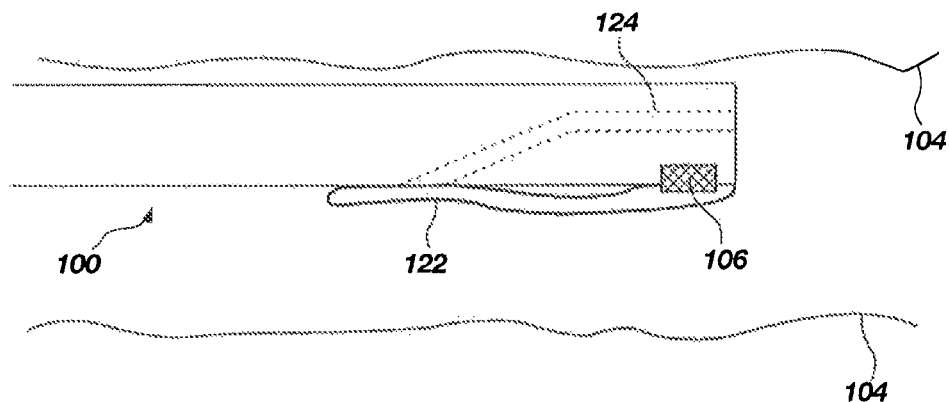
FIGS. 7a-7b are side views of one embodiment of the catheter of FIG. 5.
Figure 7B:
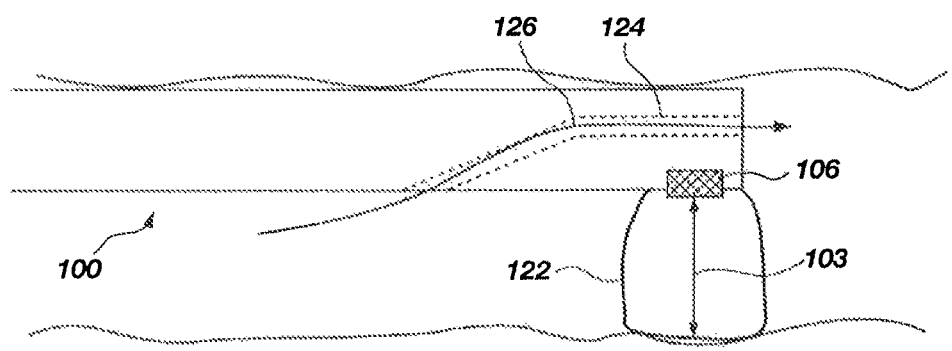

FIGS. 7a-7b illustrate a function of the transparent balloon of FIG. 5 according to one embodiment of the present invention. In one aspect of the invention, catheter 100 comprises a lumen 124 extending from a distal end of the catheter 100 to a side portion of the catheter 100. When deflated the transparent balloon 122 can be positioned along the catheter body, as shown in FIG. 7a effectively blocking the opening of lumen 124 on the lateral portion of the catheter body. As illustrated in FIG. 7b, when inflated, the transparent balloon 122 can form a transparent focal instrument wherein the distance 103 from the imaging device 106 to the outer periphery of the inflatable balloon 122 is equal to the distance 103 of the imaging device 106 to its focal plane. When in its inflated state, lumen 124 is open to the passage of fluids 126 through the vessel of the patient. Advantageously, while the distal end of the catheter 100 effectively occludes passage of any fluids 126 through the vessel of the patient, lumen 124 acts a temporary passageway for the fluids 126. While a single balloon-imaging device combination is shown, it will be understood that a plurality of such combinations can be included with the present invention. In one exemplary embodiment of the invention the catheter 100 can include four such combinations positioned around the circumference of the catheter body. Each of these four transparent balloons can be selectively inflated, either synchronously or separately in order to image the walls of a bodily passage or bodily organ. Additionally, the transparent balloon-imaging device combination can be positioned in a forward facing orientation, as shown in FIG. 5. The balloon can be inflated with air, oxygen, saline solution, or other fluid common to the art of balloon catheterization.

In another embodiment, the imaging device comprises a plurality of micro-cameras each having a different effective focal length and corresponding transparent focal instrument attached thereto. In one aspect, one of the plurality of imaging devices has a field of view that is larger than the other imaging devices. In yet another aspect, one of the plurality of imaging devices has magnification capabilities. In yet another aspect, the plurality of imaging devices may be oriented parallel to one another or may be configured in a non-parallel orientation as suits a particular application. Additional principles of operation and details of construction of GRIN lens microscope assemblies can be found in U.S. patent application Ser. No. 12/008,486 filed Jan. 1, 2008 and entitled "Grin Lens Microscope System" which is incorporated herein by reference in its entirety.

Figure 9:
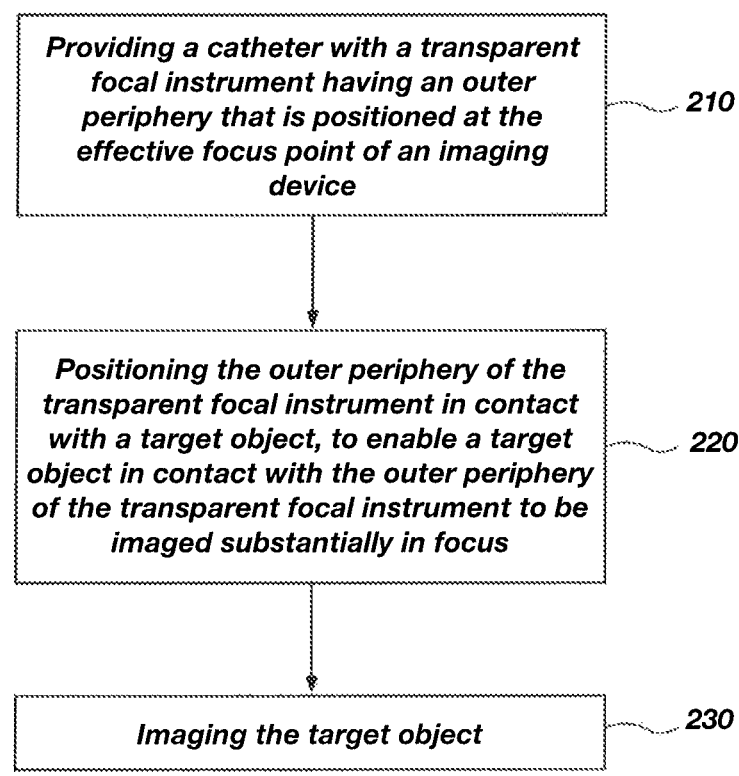
FIG. 9 is a flowchart of a method for imaging with a catheter according to one embodiment of the present invention.

FIG. 9 is a flowchart of a method for imaging with a catheter. The method first includes providing a catheter with a transparent focal instrument having an outer periphery that is positioned at the effective focal plane of an imaging device 210. The transparent focal instrument can be of a variety of configurations as described in detail above. Next, the method includes positioning the outer periphery of the transparent focal instrument in contact with a target object, to enable a target object in contact with the outer periphery of the transparent focal instrument to be imaged substantially in focus 220. Various methods and devices can be used to position the transparent focal instrument in contact with a target object. In addition to the methods and devices described above, the catheter body can be rotated around its longitudinal axis and/or the imaging device can include turning devices, such as piezoelectric actuators, for tilting and/or moving the imaging device. Additionally, the focal length of the camera can be modified in certain cameras, while the distance between the imaging device and the outer periphery of the transparent focal instrument is respectively modified. Lastly, the target object is imaged by the imaging device 230. In one embodiment of the present invention, the imaging device can be constantly imaging, so as to record and display live images to a user. Alternatively, the imaging device can include an additional feature, wherein enhanced images are selectively taken, that can be analyzed and viewed to assist in diagnosis and analysis.

Advantageously, embodiments of the present invention include a transparent focal instrument for a catheter to assist a medical practitioner to image objects that are in contact with the transparent focal instrument substantially "in focus," Thus, improved catheter imaging can be achieved by maneuvering the transparent focal instrument in contact with a target tissue/object. Such a maneuver can reduce the trial-and-error procedure of maneuvering the distal end of a catheter within a bodily passage/cavity. This can allow a user to image more tissue in less time and with higher resolution because the transparent focal instrument can be passed over a potentially diseased area or quickly and repeatedly positioned against a passage wall as it is directed down the passage. Additionally, this device can substantially enhance a catheter's ability to image critical tissue, such as potentially cancerous cells/regions in higher definition and with increased clarity, thus increasing a user's ability to diagnose and treat problems. As such this device can dramatically improve a doctor's ability to detect various illnesses and diseases at their early stages.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A catheter configured for imaging objects substantially in focus, comprising:
   a) an imaging device disposed on a distal end of the catheter, the imaging device having an effective focal plane;
   b) a transparent focal instrument coupled to the catheter, the transparent focal instrument having an outer periphery, wherein a length from the imaging device to the outer periphery of the transparent focal instrument is equal to the distance from the imaging device to the effective focal plane of the imaging device; wherein when the outer periphery is positioned at the effective focal plane of the imaging device, it enables objects in contact with the outer periphery of the transparent focal instrument to be imaged substantially in focus; and c) an open channel having a first orifice disposed about a side surface of the catheter in fluid communication with a second orifice on a distal end of the catheter, wherein the imaging device is located inside an inflatable balloon and wherein the inflatable balloon is configured to cover the first orifice of the catheter when deflated for limiting fluid communication in the open channel.

2. The catheter of claim 1, wherein the imaging device comprises a solid state imaging device including an imaging array and a graduated refractive index lens optically coupled to the imaging array of the solid state imaging device.

3. The catheter of claim 2, wherein the transparent focal instrument is coupled to the graduated refractive index lens.

4. The catheter of claim 1, wherein the imaging device includes at least two imaging devices.

5. The catheter of claim 1, wherein the imaging device is configured to image in a lateral direction with respect to a longitudinal axis of the catheter.

6. A catheter configured for imaging objects substantially in focus, comprising: a) an imaging device disposed on a distal end of the catheter, the imaging device having an effective focal plane; b) a transparent focal instrument coupled to the catheter, the transparent focal instrument having first and second positions, wherein when disposed in the second position, the transparent focal instrument has a length that is equal to the distance between the imaging device and the effective focal plane of the imaging device and is positioned at the effective focal plane of the imaging device to enable a target object in contact with an outer periphery of the transparent focal instrument to be imaged substantially in focus, wherein the transparent focal instrument comprises an inflatable balloon; and c) a channel having a first orifice disposed about a side surface of the catheter adjacent a distal end of the catheter, and a second orifice disposed about a distal end of the catheter, the first orifice being in fluid communication with the second orifice, wherein when the inflatable balloon is disposed in the second position, the channel extends from a first side of the inflatable balloon to a second side of the inflatable balloon to permit fluids within a vessel of a patient to pass from one side of the inflatable balloon to the second side of the inflatable balloon, wherein when the inflatable balloon is disposed in the first position, the inflatable balloon is configured to cover the first orifice of the catheter for limiting fluid communication in the channel.

7. A method for imaging with a catheter, comprising:

a) providing a catheter having a channel disposed therein and a transparent focal instrument, the transparent focal instrument comprising first and second positions wherein when the transparent focal instrument is disposed in the first position, the transparent focal instrument covers an opening of the channel and wherein when the transparent focal instrument is disposed in the second position, the transparent focal instrument does not cover the opening of the channel and has an outer periphery with a length equal to the length of the effective focal plane, the transparent focal instrument being positioned at an effective focal plane of an imaging device;

b) inserting the catheter into a cavity of a patient while the transparent focal instrument is disposed in the first position;

c) after inserting the catheter into the cavity of the patient, disposing the transparent focal instrument in the second position thereby occluding the cavity of the patient with the transparent focal instrument and removing the transparent focal instrument from the opening of the channel; and d) imaging a target object.

8. The method of claim 7, wherein the transparent focal instrument comprises a balloon.

9. The method of claim 8, wherein positioning the outer periphery of the transparent focal instrument includes inflating the balloon disposed on the catheter to move a distal end of the balloon in contact with the target object.

10. The method of claim 7, wherein the transparent focal instrument comprises a transparent balloon having an inflated length substantially equivalent to the effective focal plane of the imaging device.

11. The method of claim 7, wherein the imaging device is configured to image objects lateral to a longitudinal axis of the catheter.

12. The method of claim 7, wherein positioning the outer periphery of the transparent focal instrument includes inflating a balloon disposed on the catheter to move a distal end of the balloon in contact with the target object.

13. The method of claim 12, wherein the transparent focal instrument is substantially solid.

14. The method of claim 12, further comprising a plurality of imaging devices disposed about an exterior of the catheter and a plurality of balloons, each balloon enclosing a single imaging device.

* * * * *